US011931149B2

United States Patent
Pichon et al.

(10) Patent No.: US 11,931,149 B2
(45) Date of Patent: Mar. 19, 2024

(54) FMRI METHOD FOR DETERMINING BRAIN ACTIVATION PATTERNS IN RESPONSE TO ODOR ELICITED FEELINGS

(71) Applicant: FIRMENICH SA, Geneva (CH)

(72) Inventors: Aline Pichon, Princeton, NJ (US); Patrik Vuilleumier, Vessy (CH); Sylvain Delplanque, Geneva (CH); David Sander, Geneva (CH); Isabelle Cayeux, Geneva (CH); Christelle Porcherot, Geneva (CH); Maria Inés Velazco, Geneva (CH); Christian Margot, Geneva (CH)

(73) Assignee: FIRMENICH SA, Satigny (CH)

( * ) Notice: Subject to any disclaimer, the term of this patent is extended or adjusted under 35 U.S.C. 154(b) by 1017 days.

(21) Appl. No.: 16/471,533

(22) PCT Filed: Dec. 20, 2017

(86) PCT No.: PCT/EP2017/083787
§ 371 (c)(1),
(2) Date: Jun. 19, 2019

(87) PCT Pub. No.: WO2018/115107
PCT Pub. Date: Jun. 28, 2018

(65) Prior Publication Data
US 2020/0205713 A1    Jul. 2, 2020

(30) Foreign Application Priority Data
Dec. 21, 2016    (EP) .................................... 16205681

(51) Int. Cl.
*G06T 5/00*    (2006.01)
*A61B 5/00*    (2006.01)
(Continued)

(52) U.S. Cl.
CPC .............. *A61B 5/165* (2013.01); *A61B 5/055* (2013.01); *A61B 5/4011* (2013.01);
(Continued)

(58) Field of Classification Search
CPC ....... A61B 5/165; A61B 5/055; A61B 5/4011; A61B 5/16; G01R 33/4806; G06F 17/18;
(Continued)

(56) References Cited

U.S. PATENT DOCUMENTS

| 8,239,000 B1* | 8/2012 | Morris | ................... A61B 5/165 |
| | | | 600/410 |
| 2012/0220857 A1* | 8/2012 | Warr | ....................... A61P 43/00 |
| | | | 600/411 |

(Continued)

FOREIGN PATENT DOCUMENTS

JP    2015-156891 A    9/2015

OTHER PUBLICATIONS

Porcherot C et al: "How do you feel when you smell this? Optimization of a verbal measurement of odor-elicited emotions", Food Quality and Preference, Longman Scientific and Technical, vol. 21, No. 8, Doi: 10.1016/J.FQOQDQUAL .2010.03.012 (Year: 2010).*

(Continued)

*Primary Examiner* — Van D Huynh

(57) ABSTRACT

Described herein is a method of using functional MRI (fMRI) for determining brain activation patterns for a group of subjects in response to different odor-elicited feelings (i.e., conscious emotions).
A method for preparing a perfume by using the method of the present invention and a consumer product including said perfume are also described herein.

15 Claims, 9 Drawing Sheets

(51) Int. Cl.
 A61B 5/055 (2006.01)
 A61B 5/16 (2006.01)
 G01R 33/48 (2006.01)
 G06F 17/18 (2006.01)
(52) U.S. Cl.
 CPC ......... *G01R 33/4806* (2013.01); *G06F 17/18* (2013.01); *G06T 5/002* (2013.01); *G06T 2207/10088* (2013.01); *G06T 2207/30016* (2013.01)
(58) Field of Classification Search
 CPC ........... G06T 5/002; G06T 2207/10088; G06T 2207/30016
 USPC ........................................................ 600/544
 See application file for complete search history.

(56) References Cited

U.S. PATENT DOCUMENTS

| 2018/0110981 | A1* | 4/2018 | Zhou | A61N 1/0476 |
| 2019/0021645 | A1* | 1/2019 | Mochizuki | A61B 5/742 |
| 2021/0256542 | A1* | 8/2021 | Mcdaniel | G06V 40/174 |

OTHER PUBLICATIONS

International Search Report for International Application No. PCT/EP2017/083787, dated Mar. 8, 2018, 5 pages.
Fulbright et al., "Functional MR imaging of regional brain responses to pleasant and unpleasant odors", American Journal of Neuroradiology, Published Oct. 1998, vol. 19, No. 9, pp. 1721-1726.
Ischer et al., "How incorporation of scents could enhance immersive virtual experiences", Frontiers in Psychology, Published Jul. 17, 2014, vol. 5, Article 736, 11 pages.
Savic et al., "Olfactory Functions Are Mediated by Parallel and Hierarchical Processing", Neuron, Published Jun. 2000, vol. 26, pp. 735-745.
Vivancos et al., "A neuroimaging study of pleasant and unpleasant olfactory perceptions of virgin olive oil", Grasas y Aceites, Published Dec. 1, 2016, vol. 67, No. 4, 14 pages.
Zou et al., "The neural mechanism of hedonic processing and judgment of pleasant odors: An activation likelihood estimation meta-analysis". Neuropsychology, Published Jan. 1, 2016, vol. 30, No. 8, pp. 970-979.
Yeon-Kyu Kim, Characteristics of Salivary Secretary Immunoglobulin A(s-IgA) Responses to Pleasant and Unpleasant Olfactory Stimuli, Journal of Physiological Anthropology, 2009, vol. 14, No. 2, pp. 67-74.

* cited by examiner

FMRI METHOD FOR DETERMINING BRAIN ACTIVATION PATTERNS IN RESPONSE TO ODOR ELICITED FEELINGS

CROSS-REFERENCE TO RELATED APPLICATIONS

This application is a U.S. National Phase Application of PCT/EP2017/083787, filed on Dec. 20, 2017, which claims the benefit of priority to European Patent Application No. 16205681.6, filed Dec. 21, 2016, the entire contents of which are hereby incorporated by reference herein.

TECHNICAL FIELD

The present invention relates to the use of functional Magnetic Resonance Imaging (fMRI) for determining brain activation pattern(s) for a group of subjects that correspond to specific odor-elicited feeling(s) (i.e., conscious emotions), and for distinguishing activation patterns across different emotion feelings.

A method for preparing a perfume by using the method of the present invention and a consumer product comprising said perfume are also part of the present invention.

BACKGROUND OF THE INVENTION

As a result of evolution, the olfactory system has a privileged access to emotion centers of the brain, providing odors with the ability to influence the human behavior, mood and decisions.

"Odor" or "smell" usually designates the perceived sensation elicited by one or several volatile chemicals—odorants—stimulating the olfactory organ.

It has been known for a long time that there is a strong link between odors and emotions (Engen, 1976). Indeed, pleasant and unpleasant odors induce differential responses at the behavioral (Bensafi, Rouby, Farget, Vigouroux, & Holley, 2002) and physiological (Bensafi, Rouby, Farget, Bertrand, et al., 2002b; Delplanque et al., 2009) levels.

On one hand, declarative methods have been developed to provide qualitative and quantitative measures of emotional response to odorants (behavioral data). In these methods, subjects rate the intensity of various feeling descriptors upon exposure to an odorant.

On the other hand, methods providing physiological data are the subject of intense researches.

Indeed, olfaction-related literature in experimental psychology and brain imaging is undergoing an unprecedented boom, along with the development of MRI-compatible olfactometers. These technical achievements have enabled the emergence of studies characterizing the processing of olfactory stimuli at the brain level.

Physiology and declaration have often been correlated for hedonically distinct responses to odorants (for example pleasant odorant versus unpleasant odorant).

One may cite for example US2012/220857; U.S. Pat. No. 8,239,000, or "Functional MR imaging of regional brain responses to pleasant and unpleasant odors", American Journal of Neuroradiology (1998-10-01), page 1721.

In these documents, participants were requested to characterize their perception of the hedonicity/valence of the odors using a visual analogue scale varying from unpleasant/dislike/negative to pleasant/like/positive. The investigation of emotional responses to odors is limited to this core affect dimension. However, several results have seriously questioned the theoretical grounding for restricting the description of feelings to the unique scale of valence, liking, pleasantness, or acceptability. Describing odor-elicited feelings with only one dimension of valence loses most of the important qualitative differences between the affective effects of different types of odors. The odor-elicited feeling landscape is represented by several affective categories that are recurrent in many countries: disgust/irritation, happiness/well-being, sensuality/desire, energy, but also soothing/peacefulness and hunger/thirst. Each category of feelings is characterized by different representative relevant affective terms (i.e., feeling descriptor) and is evaluated with the help of a feeling intensity scale varying from not experienced or not intense at all to strongly experienced or intense.

Furthermore, US20120220857 has determined whether an odor perception statistically activates or not a specific, determined, restricted brain network (e.g., dopaminergic structures) but do not provide any quantification.

Finally, the method disclosed in US20120220857 and U.S. Pat. No. 8,239,000 specifically focuses on brain regions of interest (ROIs) that were supposedly associated with a particular affective processes—e.g., rewarding dopaminergic pathways for US20120220857, valence and arousal dimensions with bilateral inferior frontal and middle temporal gyri for U.S. Pat. No. 8,239,000 underestimating the activation of such ROIs in other non-affective processes and leaving out other pertinent brain structures that could be also activated.

Thus, up to now, no correlation between physiology and declaration has been established to compare odorants with similar hedonicity but evoking different feelings.

There is therefore a need to provide a method that could enable the correlation of specific brain activation patterns with feelings categories revealed by declarative methods for odorants with similar hedonic attributes.

The present invention now seeks to resolve these deficiencies.

SUMMARY OF THE INVENTION

In a first aspect, the present invention relates to a method for determining at least two brain activation patterns related to at least two elicited feelings for a group of subjects smelling odorants, said method comprising the following steps:
(i) Providing at least two odorants;
(ii) Submitting a group of subjects to at least two odorants, each in turn, in a MRI scanner;
(iii) Performing functional Magnetic Resonance Imaging (fMRI) of the brain of each subject smelling each odorant in turn to determine the brain activation to each odorant for each subject,
(iv) Optionally, reiterating step (iii) and identifying the average brain response to each odorant,
(v) Once step (iii) or (iv) completed, submitting the group of subjects to an evaluation of feelings evoked by each odorant based on a declarative method;
(vi) Rating and averaging the perceived intensity of at least two feeling descriptors reported by the group of subjects for each odorant based on said declarative method, wherein the feeling descriptors are not restricted to the affective dimension of valence,
(vii) Performing a statistical method using the descriptor rating scores obtained in step (vi) across the odorants to obtain a brain activation pattern associated to each descriptor.

In a second aspect, the invention relates to a method for preparing a perfume by using the method as defined above.

A third object is a consumer product comprising the perfume defined above.

A fourth object is a method enabling the identification of at least one brain activation pattern corresponding to a specific feeling category elicited by an odorant by using the method as defined above.

DEFINITIONS

Figure 1:
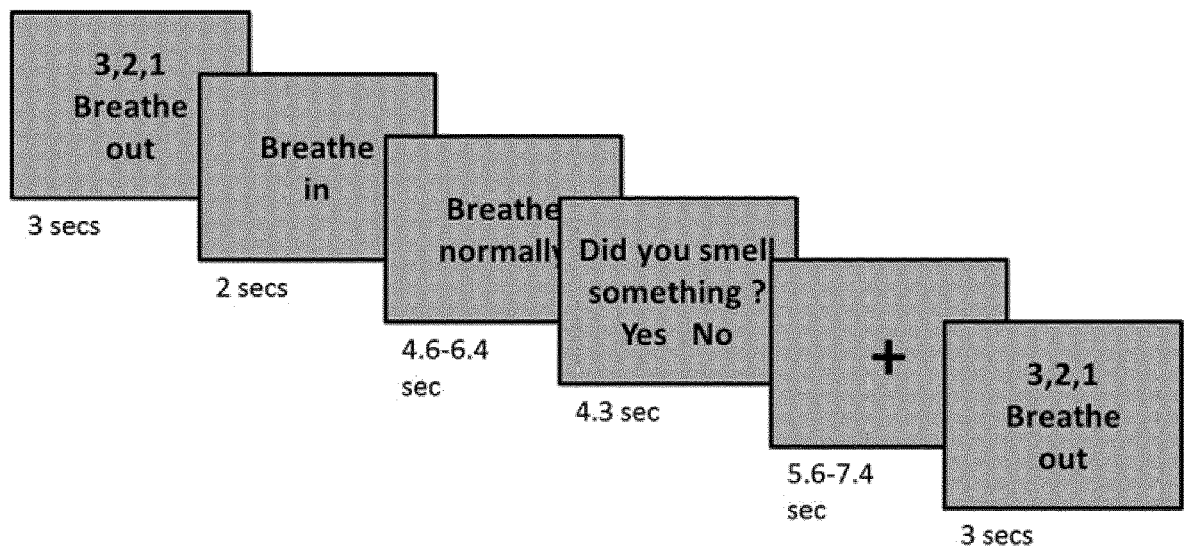
FIG. 1 represents the time course of the experiment task and odor delivery.

According to the invention:
the terms "brain activity" or "brain activation" mean response of the brain to a particular stimulus as visualized by the technique of brain imaging and resting upon the measurement of the change in blood flow,
the term "odorant" means a chemical or mixture of chemicals capable of activating odorant receptors,
the term "feeling descriptor" defines a word or series of words associated to a reported feeling (i.e., a consciously reported emotion). According to the invention, at least two feeling descriptors are not restricted to the affective dimension of valence. The affective dimension of valence is well-known by the person skilled in the art and is defined as intrinsic attractiveness/"good"-ness (positive valence) or averseness/"bad"-ness (negative valence) of an emotion. As an example, the two following descriptors pleasant and unpleasant are restricted to the unique scale of valence. By contrast, the feeling descriptors defined in the present invention are not restricted to the affective dimension of valence.
the term "declarative method» should be understood as a tool that enables a subject to rate the perceived intensity for different predetermined feelings descriptors when smelling an odorant. The declarative methods generally includes different descriptors (or categories) of feelings. One may cite for example the EOS (Emotion and Odor Scale) method. (Ferdenzi, C., Delplanque, S., Barbosa, P., Court, K., Guinard, J. X., Guo, T & Sander, D. (2013). *Affective semantic space of scents. Towards' a universal scale to measure self-reported odor-related feelings. Food Quality and Preference*, 30(2), 128-138).
The declarative method can be for example a computer-based or a paper-based questionnaire in which the subject has to rate the perceived intensity on a scale for different descriptors.

DETAILED DESCRIPTION OF THE INVENTION

The present invention provides a methodology to identify the areas of the human brain involved in the processing of feelings elicited by specific odorant stimuli or associated to them, and to distinguish between patterns corresponding to distinct feelings. Especially, the method enables the correlation of specific brain activation patterns with the intensity of odor-evoked feeling categories, regardless of shared hedonicity levels.

Therefore, a first aspect of the present invention is a method for determining at least two brain activation patterns related to at least two elicited feelings for a group of subjects smelling odorants, said method comprising the following steps:
(i) Providing at least two odorants;
(ii) Submitting a group of subjects to at least two odorants, each in turn, in a MRI scanner;
(iii) Performing functional Magnetic Resonance Imaging (fMRI) of the brain of each subject smelling each odorant in turn to determine the brain activation to each odorant for each subject,
(iv) Optionally, reiterating step (iii) and identifying the average brain response to each odorant,
(v) Once step (iii) or (iv) completed, submitting the group of subjects to an evaluation of feelings evoked by each odorant based on a declarative method;
(vi) Rating and averaging the perceived intensity of at least two feeling descriptors reported by the group of subjects for each odorant based on said declarative method, wherein the feeling descriptors are not restricted to the affective dimension of valence,
(vii) Performing a statistical method using the descriptor rating scores obtained in step (vi) across the odorants to obtain a brain activation pattern associated to each descriptor.

Step(i): Providing at Least Two Odorants

According to a particular embodiment, the odorants comprise, preferably consists of a perfume in the form of a perfuming ingredient alone or in the form of a perfuming composition including a mixture of perfuming ingredients.

By "perfume" (or also "perfume oil") what is meant here is an ingredient or composition that is a liquid, solid or semi-solid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odor. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodor counteraction, antimicrobial effect, microbial stability, insect control.

The nature and type of the perfuming ingredients do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, nitriles, terpenoids, nitrogenous or *sulphurous* heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. Examples of such solvents are dipropylene glycol (DIPG), diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

Step (ii) Submitting a Group of Subjects to Said Odorants in a MRI Scanner

Subjects

The subjects have to be free of psychiatric or neurological history and have a normal sense of smell.

According to an embodiment, the group of subjects comprises at least 5, preferably at least 10 subjects, more preferably at least 15 subjects, and even more preferably at least 20 subjects.

MRI Scanner

Any suitable MRI scanner can be used to provide the MRI brain scans (also named MRI images).

As an example, one may cite 3T whole body MRI scanner (Trio TIM, Siemens, Germany) as a suitable scanner for the present invention.

Olfactometer

According to an embodiment, the step of submitting the odorant to the subject in the MRI scanner is performed with an olfactometer.

Any olfactometer can be used as long as it is compatible with a MRI scanner to enable the supply of defined, reproducible olfactory stimuli in the nose, without tactile or thermal stimulation, in a precise and controlled manner.

The person skilled in the art would be able to select suitable concentration and duration of the stimulus as well as the interstimulus interval.

Typically:
- the concentration of the stimuli is selected in order to be perceived as similar in subjective intensity, as determined by the literature or specific evaluative tests,
- the duration of the stimulus is appropriate to elicit a specific emotion response (typically comprised between 1s and 3s),
- the interstimulus interval is sufficient to return to a neutral emotion baseline (typically comprised between 20s and 30s).

Such MRI-compatible olfactometer is for example described in the following scientific paper: Ischer, M., Baron, N., Mermoud, C., Cayeux, I., Porcherot, C., Sander, D., & Delplanque, S. (2014). How incorporation of scents could enhance immersive virtual experiences. *Frontiers in Psychology*, 5(July), 736.

According to an embodiment, subjects are equipped with a nasal cannula in each nostril connected to the olfactometer. The cannulas deliver the olfactometer output airstream into their nostrils (typically between 0.75 and 1 l/min per nostril).

According to a particular embodiment, during step ii), the stimulation is carried out with pure air and alternatively with the odorant.

Step (iii): Performing Functional Magnetic Resonance Imaging (fMRI) of the Brain MRI enables the creation of high resolution images (1 mm) of biological tissues. This is done in a non-invasive fashion, through the measurement of the nuclear magnetic resonance (NMR) signal of protons present in water. Functional MRI, based on the paramagnetic properties of hemoglobin, enables the tracing of local variations of metabolic activity in the brain with good temporal resolution (around 2 sec). The determination of brain activity is based on the Blood Oxygenation Level Dependent (BOLD) contrast whose measurement is well-known by the person skilled in the art using appropriate MRI sequences for image acquisition.

According to an embodiment, MRI data can be acquired by using a 3T whole body MRI scanner with an appropriate head coil to enhance the signal-to-noise ratio in ventral olfactory areas. Echo planar imaging (EPI) is used to sequentially acquire brain images as a series of slices.

As an example, functional images can be acquired by using a standard echo planar imaging sequence (TR/TE: 2000/20 ms, flip angle=80°, voxel size: 3.0×3.0×2.5 mm3, 3.25 mm slice spacing, 40 slices, 64×64 base resolution, field of view=192 mm). 1400-1500 volumes were acquired per session and for each participant (organized in 3 functional runs of 550-600, 425-450, and 425-450 volumes), oriented parallel to the inferior edge of the temporal and frontal lobes. Structural images can be acquired with a T1-weighted 3D sequence (TR/TI/TE: 1900/900/2.31 ms, flip angle=9°, field of view=256 mm, PAT factor=2, voxel dimensions: 1 mm, isotropic 256×256×192 voxel).

Steps (v) and (vi): Rating and Averaging the Perceived Intensity of at Least Two Feeling Descriptors for Each Odorant According to a Declarative Method Once step (iii) and optionally (iv) is completed, every subject is submitted to an evaluation of the feeling(s) evoked by each odorant based on a declarative method, using at least two feeling descriptors rated on a continuous scale (typically this can be a line scale, where the left end corresponds to "not at all" and the right end to "extremely"; the observer reports the intensity of the feeling by marking the line with a cross at the appropriate length; the scale is later digitized from 0 to 100, where 0 represents the minimum of perceived intensity and where 100 represents the maximum of perceived intensity for one descriptor).

As the step of rating the odorant according to defined descriptors is carried out after the step of capturing brain scans, one can avoid any hindsight when the subject smells the odorant in the MRI scanner.

Any declarative method that enables to map the affective space evoked by odorants by rating the intensity along at least two descriptors can be used in the present invention.

One may cite for example, Scentmove™ (Firmenich) that represents a universal emotion and odor scale.

According to an embodiment, feelings evoked by the at least two odorants are defined by at least 6 descriptors, preferably at least 9 descriptors.

According to a particular embodiment, EOS (Emotion and Odor Scale) that defines 6 different feelings categories with 6 different feeling descriptors (sensory pleasure (SP), refreshing (RF), relaxation (RX), desire-sensuality (DE), pleasant feeling (PF), unpleasant feeling (UF)) is used as declarative method.

According to an embodiment, feelings evoked by the at least two odorants are defined by at least 6 descriptors chosen in the group consisting in sensory pleasure (SP), refreshing (RF), relaxation (RX), desire-sensuality (DE), pleasant feeling (PF), unpleasant feeling (UF).

However, one can also use other descriptors such as familiarity (F; from not familiar at all to very familiar), hedonicity (H; from very unpleasant to very pleasant), or intensity (I; from not intense at all to very intense), also measured by crossing the perceived intensity value on a line scale.

Thus, according to an embodiment, the odorant is defined by at least 9 descriptors (for example from EOS or Scentmove®). According to such embodiment, the descriptors may comprise sensory pleasure (SP), refreshing (RF), relaxation (RX), desire-sensuality (DE), pleasant feeling (PF), unpleasant feeling (UF), familiarity (F), hedonicity (H) and intensity (I).

According to an embodiment, the group of subjects is submitted to at least 5 odorants, preferably at least 10 odorants.

Each of steps (ii) to (vi) can be repeated to obtain more accurate results.

Step (vii) Performing a Statistical Method so as to Obtain a Brain Activation Pattern Associated to Each Descriptor The analysis of the fMRI data obtained can be performed by using any well-known statistical methods.

According to an embodiment, the statistical method used is a parametric regression analysis.

According to an embodiment, the analysis of the fMRI data is carried out by using Statistical Parametric Mapping (SPM; reference: Statistical Parametric Mapping: The Analysis of Functional Brain Images, 1st Edition; Editors W. Penny, K. Friston, J. Ashburner, S. Kiebel, T. Nichols, Academic Press 2006), a program enabling the processing of the raw data into images and statistical analyses.

According to an embodiment, a step of preprocessing is performed before the step of performing a parametric regression analysis, said preprocessing comprising the following step:

(i) realignment of the images to a reference scan,
(ii) mapping each coordinate of subject's brains onto the corresponding coordinates of a standard brain template (normalization), and
(iii) smoothing the images As an example, during the preprocessing:
(i) the images undergo realignment to a reference scan, usually the first acquired volume, by estimating the six parameters (translation and rotational movements in the x, y, and z spatial directions) of an affine "rigid-body" transformation that minimizes the difference between each image and the reference. 6 corresponding vectors, containing one value per acquired volume, are generated, to be later used to refine subsequent analytical steps. The images are therefore corrected for head movements (which occur despite the physical restraints and instructions to participants).
(ii) the second step, normalization, consists in mapping each coordinate of subject's brains (voxels) onto the corresponding coordinates of a standard brain template, in order to compensate individual anatomical differences. One can use the Montreal Neurological Institute (MNI) template, consisting in an average of 305 humans.
(iii) images are smoothed, for example with a Gaussian kernel (usually 8 mm full width half-maximum), which enables the gradual redistribution activity of one central voxel's activity to its neighbors.

The data can be analyzed using the general linear model (GLM) framework implemented in the Statistical Parametric Mapping (SPM).

According to an embodiment, for each subject, and each functional run, the analysis is focused on the onset time of the odorant intake (e.g. using a "breath in" instruction). This time onset can be modeled as a delta function (event of duration zero) convolved with the canonical hemodynamic response function. These onsets are used to generate different regressors that can then be entered in the fMRI regression analysis, with one regressor for each of the emotion feelings, plus those for any control events. Finally, movement parameters (e.g. x, y, and z translations [in millimeters] and pitch, roll, and yaw rotations [radiants] estimated from realignment steps) can be included as covariates of no interest to account for movement-related variance. Low-frequency signal drifts are then filtered out from the time series (typically by using a cutoff period of 128 s).

To determine a brain activation pattern associated with a descriptor, the method of the present invention allows performing parametrical regression analyses of the brain response using the descriptor rating scores across all the odorants.

According to an embodiment, parametric maps are calculated at a first level for each subject and each of the descriptor scores, with odorant onset as a single event type, and then entered into separate random-effect contrast (one-sample t-test) at a second level.

In other words, during the first level analysis, effects are estimated for each individual subject, and during the second level analysis, the effects estimated in the first level analysis are compared across different subjects. Different regressors derived from independent emotion rating scores are used to perform different regression analyses and identity patterns of activity corresponding to the intensity of each category of odor-evoked feelings.

The general linear model (GLM) is the most commonly employed to fit the functional signal from each individual voxel according to the following equation: $Y = X \cdot \beta + \varepsilon$, where Y is the BOLD signal, and X represents the design matrix, which comprehends all regressors or variables that might explain changes in the BOLD signal. These regressors can be of interest (e.g. feeling rating scores), i.e., variables/ conditions that are intentionally manipulated, or of no interest, i.e., nuisance variables that are not the main objective of the experimental manipulation but might nevertheless influence the signal (e.g., the movement parameters defined during the realignment, instruction events, etc).

Physiological variations related to cardiac and respiratory activity have a direct effect on the BOLD signal, and are filtered out from the time series, e.g. using a standard high pass filter of $1/128$ Hz or additional regressor factors as needed. Thus, experimental constraints particular to olfactory experiments (e.g. specific sniffing pattern) often necessitate the separate modelling of cardiac and respiratory noise as nuisance regressors.

In the GLM, each regressor X represents a lot of event onsets modelled through a delta function and convolved with a canonical hemodynamic response function to mimic the induced BOLD response. The GLM estimates the parameters $\beta$, representing the degree to which Y is explained by each regressor X, together with the error term c, which is the difference between the observed data and the model's prediction. More specifically $\beta$ estimates reflect the increase of neural signal during each condition of interest relative to the implicit baseline, which is in turn defined as the activity when all regressors X are set to $\beta$ (e.g., the pauses between one experimental trial and the subsequent).

The second level assesses the common patterns of activation across subjects. The individual $\beta$ parameters resulting from the first level analysis are entered into a second level (random-effects) analysis, with different individual subjects modeled as random factors, to account for functional interindividual variability. As for the case of the first level analysis, also the second level analyses lead to parameter estimates $\beta$, which represent the estimated activity of each condition across the overall population, and an error term $\epsilon$, which represents the unexplained variance. The statistical significance of one parameter $\beta$, or of the combination of many $\beta$s, is tested through contrast matrixes, which lead to t-tests or F-tests.

T-tests are used to assess the significance of individual contrasts through the formula IA $$\frac{c\beta}{Std(c\beta)}, \quad (IA)$$

which represents the ratio between the magnitude of a contrast $c\beta$ and its estimated standard error.

F-tests instead compare the goodness of fit of the model (i.e., the residual sum of squares, $\Sigma\epsilon^2$) with that of a reduced model in which multiple conditions (described by corresponding contrast matrixes) are missing: the resulting F value represents the ratio between the variability explained by the contrasts of interest and the unexplained variability F having the following formula $$F = \frac{\sum \epsilon^2 \text{ reduced model} - \sum \epsilon^2 \text{ full model}}{\sum \epsilon^2 \text{ full model}}$$

Each test employed will lead to a statistical parametric map, describing the magnitude of ts-(T-tests) and Fs (F-tests) (plus the corresponding significance p values) in each brain coordinate.

In the present invention, parametric regressors used to perform a GLM analysis of brain activation patterns can be derived from descriptors that are identified with an appropriate behavioral measure (using a declarative method) and defined as independent dimensions or categories of odor-evoked feelings (using descriptive or multivariate statistics). Using the so-calculated regressors as parametric factors in the GLM analysis of fMRI data allows the identification of separate brain activation patterns for distinct feeling categories and the determination of their modulation as a function of the intensity of the experienced feeling across odorants and across subjects.

The present method provides a parametric quantification of the involvement of the different feelings related networks. Thus, the method not only enables one to determine feelings related brain networks but also the degree of activation of such networks.

Furthermore, the current approach examines large-scaled neuronal networks, without a priori specific assumptions, using whole brain analyses which allow a better refinement of feelings related brain networks (i.e., reducing false negative errors).

It has been shown that the declarative method is a robust tool to determine the elicited feeling for a group of subject smelling odorants since the declarative response is highly correlated to physiological data (brain imaging).

Thus, another object of the present invention is a method for preparing a perfume by using the method of the present invention.

In one aspect, the present disclosure provides a method,
  wherein the method generates a perfuming composition that elicits a specific odor-elicited feeling in a subject, and
  wherein the method comprises the steps of:
    a. receiving, by at least one computer processor executing specific programmable instructions configured for the method, data comprising at least one specific odor-elicited feeling elicited by a perfuming raw ingredient from a plurality of perfuming raw ingredients;
    b. receiving, by the at least one computer processor, input data comprising a specific odor-elicited feeling from the subject;
    c. selecting, by the at least one computer processor, based in the input data, at least one perfuming raw material that elicits the specific odor-elicited feeling; and
    d. formulating, based on the selection, by the at least one computer processor, the perfuming composition that elicits the specific odor-elicited feeling in the subject.

In one aspect, the data comprising at least one specific odor-elicited feeling elicited by a perfuming raw ingredient from a plurality of perfuming raw ingredients is generated by a method,
  wherein method determines at least two brain activation patterns related to at least two elicited feelings for a group of subjects smelling odorants,
  wherein the method comprises the steps of:
    a. providing at least two odorants;
    b. submitting a group of subjects to at least two odorants, each in turn, in a MRI scanner;
    c. performing functional Magnetic Resonance Imaging (fMRI) of the brain of each subject smelling each odorant in turn to determine the brain activation to each odorant for each subject;

d. optionally, reiterating step (c) and identifying the average brain response to each odorant;
e. submitting the group of subjects, once step (c) or (d) completed, to an evaluation of feelings evoked by each odorant based on a declarative method;
f. rating and averaging the perceived intensity of at least two feeling descriptors reported by the group of subjects for each odorant based on said declarative method, wherein the feeling descriptors are not restricted to the affective dimension of valence; and
g. performing a statistical method using the descriptor rating scores obtained in step (f) across the odorants to obtain a brain activation pattern associated to the descriptor, wherein the brain activation pattern associated to the descriptor is stored by the at least one computer processor as the data comprising at least one specific odor-elicited feeling elicited by a perfuming raw ingredient.

In one aspect, the data comprising at least one specific odor-elicited feeling elicited by a perfuming raw ingredient from a plurality of perfuming raw ingredients is generated by a subject's response to a questionnaire in which the subject rates the perceived intensity elicited by a perfuming ingredient for different descriptors, selected from the group consisting of: sensory pleasure (SP), refreshing (RF), relaxation (RX), desire-sensuality (DE), pleasant feeling (PF), unpleasant feeling (UF), familiarity (F), hedonicity (H) and intensity (I).

Still another object of the invention is a consumer product comprising said perfume.

According to an embodiment, the consumer product is in a form of a fine fragrance product, a laundry care product, a home care product, a body care product, a skin care product, an air care product, or a hygiene product.

Another object of the invention is a method enabling the identification of at least one brain activation pattern corresponding to specific feeling categories elicited by an odorant by using the method as defined above.

The invention will now be further described by way of an example. It will be appreciated that the invention as claimed is not intended to be limited in any way by this example.

Example 1

Method of the Present Invention

I—Material and Method
Group of Subjects

Seventeen right-handed, nonsmoking participants (19-33 years old, 9 females) with a self-reported normal sense of smell took part in this study. As olfactory affective perception varies as a function of culture, participants were required to be native French speakers and to have spent most of their life in Switzerland or in France, so that they could comply with the geographical background of the Geneva Emotion and Odor Scale (GEOS).

Subjects were free of psychiatric or neurological history and had normal or corrected-to-normal vision. The experiment was approved by the local ethics committee and conducted according to the Declaration of Helsinki.
Olfactory Stimuli Twelve varied pleasant and unpleasant odorants provided by Firmenich S. A. (table 1) were used to elicit olfactory stimulation. The odors were stored in synthetic fiber tampons (1.3 cm diameter, such as those provided by Burghart Messtechnik GmbH that were filled with a given odorant diluted in odorless DIPG. An additional tampon with DIPG only (and without odor) was used as a control.

Each tampon was enclosed in an individual glass vial (22 mm diameter×120 mm high) to avoid cross odor contamination. The names of the odors were not provided to the participants, because verbal inputs do influence odor perception.

TABLE 1

Odorant stimuli with respective dilutions in dipropylene glycol (DIPG) and average basic odor feature ratings: familiarity, intensity, and hedonicity

| Odorant name | Concentration | Familiarity | Intensity | Hedonicity |
|---|---|---|---|---|
| Caramel (caramel yogurt) | 20% | 57.4 | 50.1 | 54.8 |
| Ariana (laundry soap) | 1% | 60.5 | 43.6 | 60.2 |
| Grapefruit | 20% | 65.4 | 66.0 | 65.4 |
| Floral strawberry | 5% | 65.9 | 59.3 | 62.3 |
| Lilac | 10% | 54.4 | 41.1 | 63.1 |
| Eucalyptus | 20% | 79.9 | 78.4 | 68.7 |
| Ethylmaltol (caramel) | 20% | 48.7 | 47.6 | 57.5 |
| Eucalyptol (eucalyptus) | 20% | 69.3 | 60.0 | 64.2 |
| D-Limonene (orange) | 10% | 36.9 | 39.5 | 41.1 |
| Isovalerianic acid (sweaty feet) | 1% | 43.3 | 49.8 | 12.7 |
| Butyric acid (rancid butter, vomit) | 5% | 44.3 | 32.2 | 29.3 |
| Blue cheese + isovaleric acid | 10% + 1% | 41.1 | 73.7 | 11.9 |
| Control | NA | 46.3 | 9.7 | 48.2 |

Odor Delivery

Odorants were delivered via a custom designed MRI compatible olfactometer. The device consists of a nonmetallic array of 28 odorant-containing glass tubes placed on a plastic support in the MRI acquisition room as close as possible to the participant. The odorant sources are connected via a mixing chamber by short (<60 cm) anti-adhesive polytetrafluoroethylene tubes to the intranasal cannula. Each glass vial is pressure fed by a corresponding computer-controlled air valve located in the control room. The latter is switched on to send an odorant stimulus. During control conditions, extra inter stimulus interval air valves send clear air to the nose. The whole system, connected to the medical air supply of the building, enables a precise and constant clean delivery of air at 0.75 l/min, with no detectable flow variation during odorant trigger.

Experimental Procedure

Participants underwent 2 identical fMRI sessions of approximately 1 h each. Each session, divided into 3 functional runs, was separated from the other by at least a day and a maximum of 10 days. To rule out intersession hunger effects, subjects came at the same time of the day for the 2 sessions and did not eat or drink anything 30 min before the experiment. After signing a consent form and undergoing a thorough check for MRI compatibility, subjects were brought into the MRI room and equipped with the physiology measurement apparatus, as well as with a nasal cannula connected to the MCO to deliver the olfactory stimuli. They were also provided with a response button box to perform the task.

The overall experiment comprised 260 experimental trials (130 per session, organized into 3 functional runs of 50, 50, and 30 trials), corresponding to each of the 12 odors plus the odorless control, administered 20 times in total via the computer-controlled MCO in pseudo-randomized order to avoid any presentation order confound. To maximize olfactory perception, at each experimental trial, the participants had to breathe in a cued fashion as follows: breathe out for 3 s before each olfactory stimulus during a 3 s countdown (3, 2, 1), and then inspire for 2 s during odorant delivery (see FIG. 1), and then breathe normally again. The latter instruction was presented for a period of time ranging from 4.6 to 6.4 (average 5.5) s.

Subjects subsequently had to perform a simple detection task within 4.3 s in order to verify whether the odor was detected. In particular, they were asked to answer the question, "Did you smell something?" by pressing 1 of 2 keys corresponding to "yes" or "no" with their dominant hand. A fixation cross ranging from 5.6 to 7.4 (average 6.5) s was then presented during the intertrial interval. Each trial lasted on average 21.3 s to minimize habituation and to avoid cross-contamination between sequential presentations of odorants. To further ensure minimal ambient air pollution, the MRI inbuilt air extractor was switched on, thus ensuring that the MRI room air was globally renewed every 3.07 to 4.13 min (renewal rate: 1450 $m^3 \cdot h^{-1}$ to 1950 $m^3 \cdot h^{-1}$). The experiment was conducted using E prime 2.0 software (Psychology Software Tools).

Behavioral Ratings: Hedonicity, Familiarity, Intensity, and GEOS

Following the MRI scanning session, subjects were engaged in an additional experimental session in which they had to rate the 12 odors according to 9 different emotional descriptor scales ranging from 0 to 100, and averaged across participants (n=17):

6 GEOS descriptors→SP=Sensory Pleasure, RF=Refreshing, RX=Relaxation, DE=Desire, PF=Pleasant Feeling, UP=Unpleasant Feeling.
 3 other descriptors→F=Familiarity, H=Hedonicity and I=Intensity dimensions.

MRI Data Acquisition

MRI data were acquired at the Brain and Behaviour Laboratory of the University of Geneva, by using a 3T whole body MRI scanner (Trio TIM, Siemens, Germany) with the device 32 channel head coil to enhance the signal-to-noise ratio in ventral olfactory areas. Given that the cued-breathing protocol could generate potential extra movement artifacts, special care was given to restrict head movement with foam pillows. Visual stimuli were presented on a back projection screen inside the scanner bore by using an LCD projector (CP-SX1350, Hitachi, Japan).

Structural images were acquired with a T1-weighted 3D sequence (TR/TI/TE: 1900/900/2.31 ms, flip angle=9°, field of view=256 mm, PAT factor=2, voxel dimensions: 1 mm, isotropic 256×256×192 voxel). Functional images were acquired by using a standard echo planar imaging sequence (TR/TE: 2000/20 ms, flip angle=80°, voxel size: 3.0×3.0× 2.5 mm3, 3.25 mm slice spacing, 40 slices, 64×64 base resolution, field of view=192 mm). For each participant, 1400-1500 volumes per session (organized in 3 functional runs of 550-600, 425-450, and 425-450 volumes) were acquired oriented parallel to the inferior edge of the temporal and frontal lobes.

fMRI Analysis

Preprocessing fMRI data were processed and analyzed with SPM8 software (Statistical Parametric Mapping, Wellcome Trust Center for Imaging, London, UK; http://www.fillon.ucl.ac.uk/spm). For each subject and for each functional run, the first 3 volumes were discarded. The remaining images were corrected for head movement between scans by an affine registration. The resulting functional images were aligned to the T1-weighted anatomical image through rigid-body registration. The anatomical image was then spatially normalized to the Montreal Neurological Institute single-subject template by using the unified segmentation function in SPM8. The resulting deformation field was then applied to all functional images, which were then resliced (voxel size: 2×2×2 mm) and spatially smoothed with a standard 8 mm full-width at half-maximum Gaussian filter.

Analysis of Odor-Evoked Activity

The preprocessed data were analyzed by using the general linear model (GLM) framework implemented in SPM. For each subject, and each functional run, the analysis was focused on the onset time of the "breathe in" instruction, corresponding to the estimated moment (3200 ms after switching on the valve aperture) in which the odorant reached the participant's nose. This time onset was modeled as a delta function (event of duration zero) convolved with the canonical hemodynamic response function. As odors and control detection were generally high (see Results section), no distinction was made between correct and erroneous events. This resulted in 13 different regressors, one for each of the 12 odors plus control events. Finally, the 6 differential movement parameters (x, y, and z translations [in millimeters] and pitch, roll, and yaw rotations [radiants]) were included as covariates of no interest to account for movement-related variance. Low-frequency signal drifts were filtered by using a cutoff period of 128 s.

The parameter estimates associated with homologous conditions in different functional runs were averaged together through contrast matrices. This led, for each subject, to 13 contrast images, which were entered into a second-level flexible-factorial design with "odor identity" as a within-subject factor of 13 levels (12 odors, plus a control) and "subject" as a random factor, using a second-level GLM. In modeling the variance components, the within-subject factor was allowed to have unequal variance across levels, whereas equal variance was instead assumed for the "subject" factor. This analysis served the purpose of assessing, as a manipulation check, the neural responses associated with the occurrence of an odorant compared with the odorless control (main effect of odor perception), as well as the differential activity between different kinds of odors (e.g. valence effect: pleasant vs. unpleasant odors).

Parametrical Analysis of Post-Scan Ratings

The model described above allows inspection of putative differences in activity associated with different kinds of odors, but does not permit us to determine the correlates of olfactory-elicited feelings or to compare the emotional characterization by GEOS in relation to pleasantness alone at the neural level. To this end, a methodology in which the neural responses associated with the detection of odorant stimuli were analyzed in relation to the ratings that each subject gave about each kind of odor in the post-scan session, was used. This was achieved through GLMs in which the 12 different kinds of odors were modeled as part of the same condition, but independently from odorless control events. The data from post-scan scores were then entered into the GLM as parametrical regressors associated with the occurrence of each odor event. Critically, 9 independent GLMs, each with only 1 parametrical regressor, were ran to test the effect of either one of the 6 categories of GEOS or one of the 3 basic odor features: H, F, I. Although the odors were selected and delivered at concentrations that ensured global iso-intensity of the stimuli, putative effects of F and I were analyzed, as well as additional measures for inter-subject perception variability. No parametrical modulation was associated with the control condition, given the general consensus among the participants' answers to an absence of stimulus. For each participant, and for each GLM, parameter estimates associated with the parametric regressors in different functional runs were averaged together through contrast matrices. This yielded 9 contrast images per participant (one for each GLM), which were entered into a second-level flexible-factorial design with "odor features" as the within-subject factor with 9 levels. Of note is that one did not enter all 9 rated dimensions (6 GEOS, plus H, F, and I) into the same GLM, in order to avoid serial orthogonalization (as implemented in first-level models in SPM) and subsequent variation in results according to the order of the parameters in a unique model. The use of separate models allowed a better and unbiased account of each emotional parameter, comparable to what would have been obtained if the dimensions had been uncorrelated.

In all analyses, it is considered that reliable activations are those exceeding a height threshold corresponding to $P<0.001$ uncorrected, with a cluster size of at least 3 continuous voxels. Results were constrained to grey matter only, with a strictly inclusive binary mask (threshold>0.33) generated from the canonical grey matter image (grey.nii) used for segmentation during preprocessing in SPM.

II—Results

II-1—Bevavioral Results—Descriptor Rating Scores

The emotional ratings of odors (post scanning) were generally similar across participants for all emotion categories (average Cronbach's alpha=0.89—see table 2).

TABLE 2

Item Reliability (SP = Sensory Pleasure,
RF = Refreshing, RX = Relaxation,
DE = Desire-Sensuality, PF = Pleasant Feeling,
UF = Unpleasant Feeling, F = Familiarity,
H = Hedonicity, I = Intensity).

| Feeling descriptors | Cronbach's alpha | Intraclass correlation (average measures) |
|---|---|---|
| SP | 0.84 | 0.29 |
| RF | 0.93 | 0.50 |
| RX | 0.91 | 0.42 |
| DE | 0.80 | 0.23 |
| PF | 0.92 | 0.50 |
| UF | 0.93 | 0.54 |
| F | 0.88 | 0.33 |
| H | 0.94 | 0.54 |
| I | 0.87 | 0.33 |

To investigate the degree to which different odors elicited differential subjective emotional reactions, separate ANOVAs for H, F, and I ratings with "odors" as the unique within-subject factor with 12 levels were performed. In all ANOVAs, the main effect "odor" was found to be significant ($Fs(11,176) \geq 9.38$; $Ps<0.0001$).

Figure 2A:
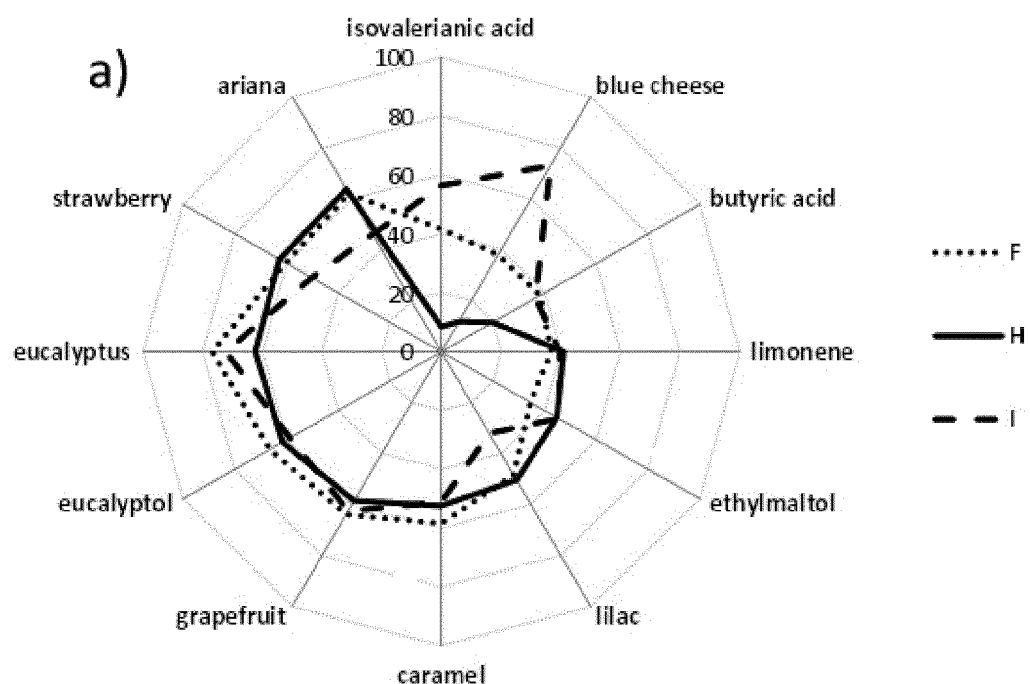
FIG. 2a represents the odor average ratings of the descriptors: F=Familiarity, H=Hedonicity and I=Intensity for each odorant.

FIG. 2a depicts the average H, I and F ratings of each odor category.

Hedonicity ratings ranged from 8 (isovaleric acid, lowest hedonicity) to 65 (ariana, the highest hedonic ratings). Familiarity ranged from 34 (ethylmaltol, the least familiar) to 76 (*eucalyptus*, the most familiar), although it should be stressed that no odor was considered as completely unknown (i.e. ratings approaching 0, $ts(16) \geq 7.96$, $Ps<0.05$).

Finally, Intensity ranged from 32 (lilac, the least intense) to 72 (*eucalyptus*, the most intense), although each of the 12 odors was perceived as more intense than the control condition ($ts(16) \geq 4.17$ $Ps<0.05$).

Figure 2B:
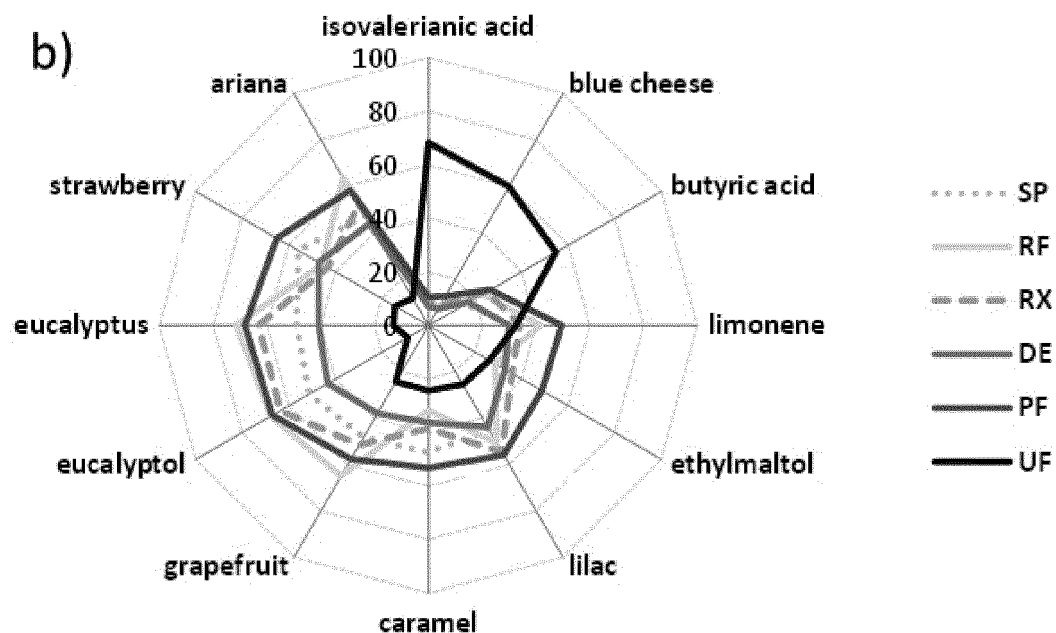
FIG. 2b represents the odor average ratings of the GEOS descriptors: SP=Sensory Pleasure, RF=Refreshing, RX=Relaxation, DE=Desire, PF=Pleasant Feeling, UP=Unpleasant Feeling for each odorant.

6 separate ANOVAs were also conducted to assess formally whether the odors elicited a variegated pattern of feelings according to GEOS ratings. All 6 ANOVAs had a significant odor effect ($Fs(11,176)>6.54$; $Ps<0.0001$), showing that the olfactory stimuli were effective in eliciting a variegated pattern of feelings (see FIG. 2b) and were suitable for a parametrical analysis in fMRI.

II-2—fMRI Results

As a manipulation check, cerebral regions were firstly identified responsive to olfactory stimulation by comparing all events in which an odor was delivered with respect to a control odorless event (Odor vs No-Odor, O>NO). This contrast revealed robust activations in the lateral OFC, as well as in the amygdala and hippocampus (FIG. 3a and Table 3), all involved in olfactory processing and encompassing both primary and secondary olfactory areas.

Figure 3:
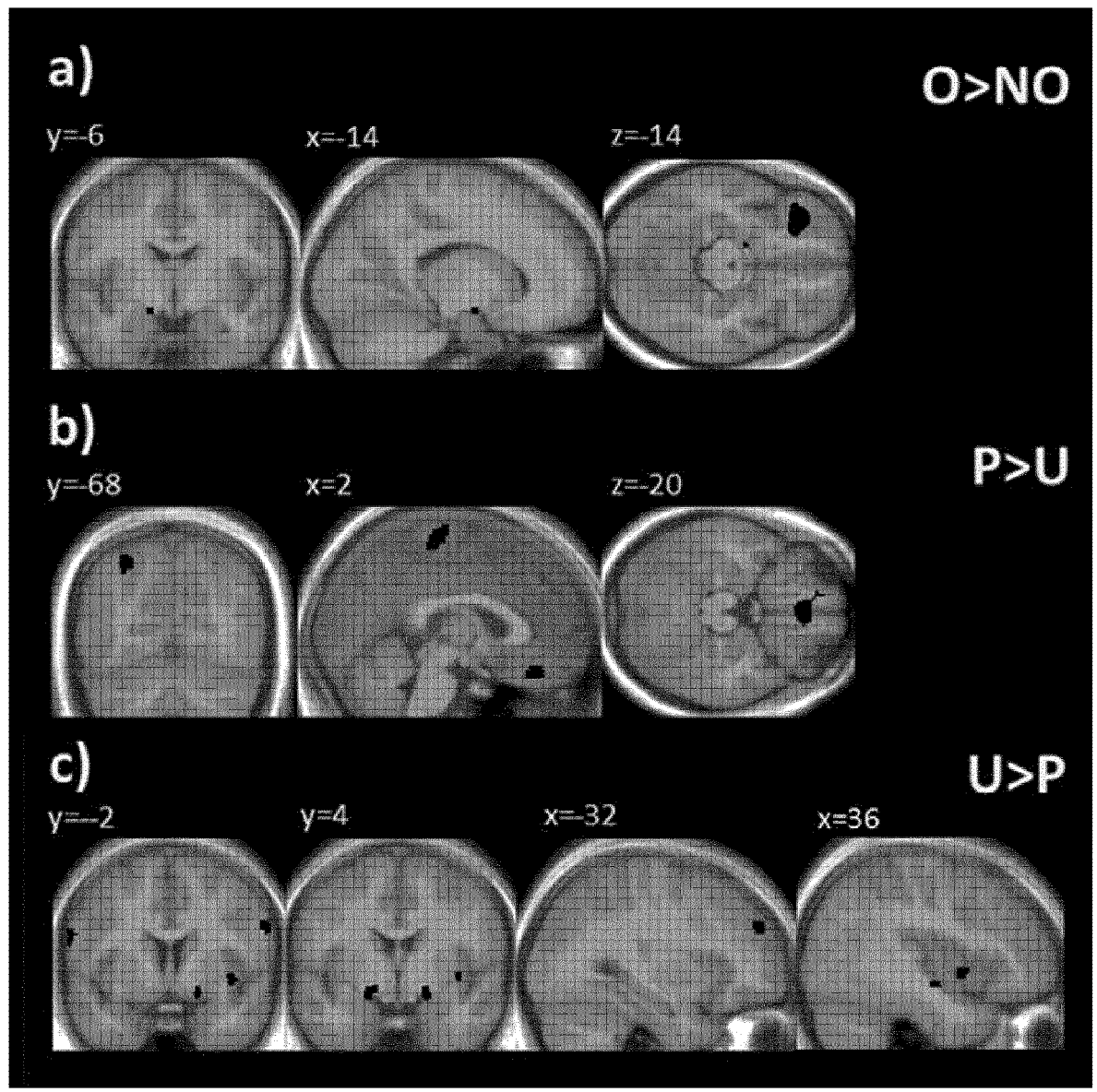
FIG. 3 shows brain sections displaying differential activity for the odor>non-odor (O>NO), pleasant>unpleasant (P>U) and unpleasant>pleasant (U>P) contrasts. Activations are overlaid on an anatomical brain scan, which is the average of that from all participants in this study (height level threshold corresponding to P<0.001, whole brain [WB], uncorrected).

To test for global emotional effects, one then contrasted odors that were a priori defined as positive vs. negative (FIG. 3b,c and Table 3). Pleasant odors (P) relative to Unpleasant odors (U) elicited greater activity in the medial OFC (typically associated with positive odor valence), but also in the inferior frontal gyrus (IFG extending to the lateral OFC), the medial frontal gyrus and supplementary motor area (SMA), the superior parietal lobule, as well as the posterior cerebellum. The opposite contrast (Unpleasant vs. Pleasant odors) yielded bilateral increases in the anterior insula (involved in disgust), plus the piriform cortex (PirC) and parahippocampal gyrus, left amygdala, right dorsolateral prefrontal cortex (dlPFC), and right superior temporal gyrus (STG). Additional clusters were also found in motor-related areas such as the precentral gyrus, the cerebellum, the pons, and the midbrain.

TABLE 3

Activation coordinates for the odor > non–odor (O > NO), pleasant > unpleasant (P > U), and unpleasant > pleasant (U > P) contrasts

| Contrast | Region | Extends to | Lat. | Cl. Size | z value | x | y | z |
|---|---|---|---|---|---|---|---|---|
| O > NO | IFG/lateral OFC | | L | 424 | 5.14 | −32 | 32 | −14 |
| | IFG pars triangularis | | L | | 3.73 | −42 | 32 | 2 |
| | IFG pars triangularis | | L | | 3.58 | −48 | 26 | −8 |
| | Amygdala | Hipp. | L | 8 | 3.24 | −14 | −6 | −14 |
| P > U | Medial FG/SMA | | R | 173 | 4.26 | 4 | −26 | 64 |
| | Medial OFC/Gyrus rectus | | L | 161 | 4.09 | −2 | 34 | −22 |
| | Medial OFC | | L | | 3.27 | −12 | 50 | −20 |
| | IFG/frontopolar | | L | 33 | 3.31 | −30 | 50 | 4 |
| | IFG/lateral OFC | | L | | 3.25 | −36 | 50 | −4 |
| | SPL | | L | 63 | 3.67 | −30 | −68 | 50 |
| | Cerebellum posterior lobe | | R | 5 | 3.16 | 44 | −64 | −40 |

TABLE 3-continued

Activation coordinates for the odor > non-odor (O > NO), pleasant > unpleasant (P > U), and unpleasant > pleasant (U > P) contrasts

| Contrast | Region | Extends to | Lat. | Cl. Size | z value | x | y | z |
|---|---|---|---|---|---|---|---|---|
| U > P | Amyg. | | L | 68 | 3.78 | −20 | −6 | −10 |
| | Frontal PirC. | Amyg./PHG | L | | 3.29 | −16 | 2 | −12 |
| | Frontal PirC. | Amyg./PHG | R | 40 | 3.61 | 16 | 0 | −12 |
| | SFG/dlPFC | | R | 72 | 3.70 | 32 | 48 | 30 |
| | PreCG | | L | 22 | 3.57 | −62 | 4 | 24 |
| | PreCG | | R | 36 | 3.54 | 60 | 6 | 30 |
| | STG/planum polare | | R | 25 | 3.60 | 42 | −12 | −12 |
| | Anterior insula | | R | 34 | 3.51 | 40 | 4 | −4 |
| | Anterior insula | | R | 4 | 3.20 | 34 | 8 | 0 |
| | IFG frontal operculum | | R | 5 | 3.17 | 42 | 16 | 8 |
| | Cerebellum anterior lobe | | R | 59 | 3.80 | 12 | −42 | −34 |
| | Cerebellum anterior lobe | | L | 7 | 3.35 | −16 | −36 | −32 |
| | Pons | | R | | 3.25 | 18 | −34 | −36 |
| | Midbrain | | L | 24 | 3.79 | −8 | −22 | −10 |

Note:
All regions exceed height threshold corresponding to P < 0.001 (uncorrected).
Coordinates (in standard Montreal Neurological Institute [MNI] space) refer to maximally activated foci:
x = distance (mm) to the right (+) or the left (−) of the midsagittal line;
y = distance anterior (+) or posterior (−) to the vertical plane through the anterior commissure (AC);
z = distance above (+) or below (−) the inter-commissural (AC-posterior commissure (PC)) line.
L and R refer to the left and right hemisphere, respectively.
Amyg. and Hipp. refer to amygdala and hippocampus, respectively.

Parametrical Effects

The global statistical strategy was to perform 9 separate parametrical regression models, on the basis of individual H, F, I, and GEOS rating scores for each odor calculated at the first level, in order to assess neural correlates related to odor-elicited subjective feelings.

Effects of Hedonicity

The previous results revealed differential activity between different kinds of odorants, thus converging with earlier studies in mapping neural structures involved in olfactory perception, as well as structures differentially engaged in positive, relative to negative, substances. These effects, however, do not take into account the subjective evaluation of the odorants and the idiosyncratic differences across participants. To overcome this limitation, it was searched for regions that, regardless of the odorant used, display an activity that is parametrically modulated by the values in post-scan ratings.

Figure 4:
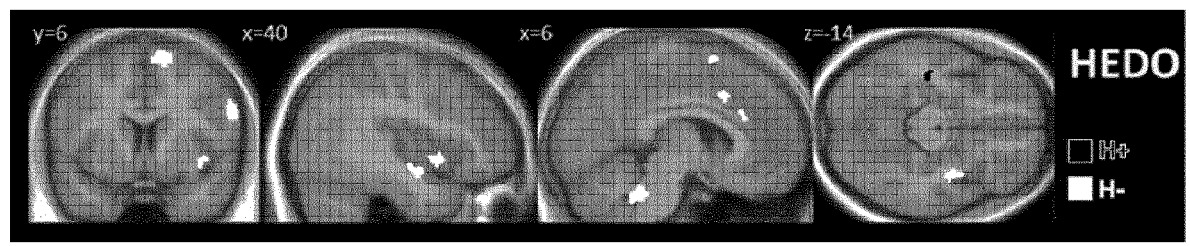
FIG. 4 represents the regression analysis for Hedonicity. (black) Positive correlation. (white) Negative correlation. Whole brain (WB), P=0.001, uncorrected.

As a first step, the neural correlates of olfactory hedonicity (H) were assessed. In partial reflection of what was found for the contrast U>P, it was found that the perigenual anterior and anterior middle cingulate gyri, right ventral anterior insula, SMA, dlPFC, and left inferior parietal lobule (IPL) and cerebellum exhibited an activity that decreased with hedonicity ratings (H−) (see FIG. 4, white blobs, and Table 4). Conversely, the neural activity in the right medial temporal lobe increased with hedonicity ratings (H+) (FIG. 4, black blobs, and Table 4).

TABLE 4

Brain areas correlating with hedonicity

| Contrast | Region | Extends to | Lat. | Cl. Size | z value | x | y | z |
|---|---|---|---|---|---|---|---|---|
| H+ | Medial temporal lobe | STS | L | 3 | 3.30 | −38 | −22 | −14 |
| H− | dlPFC | PreCG | R | 128 | 4.14 | 62 | 6 | 26 |
| | SFG/SMA | | R | 159 | 4.12 | 16 | 8 | 62 |
| | IFG/inferior frontal operculum | PreCG | R | 20 | 3.34 | 60 | 10 | 12 |
| | Cerebellum anterior lobe | | R | 186 | 4.27 | 10 | −42 | −30 |
| | Cerebellum anterior lobe | | L | 73 | 3.91 | −16 | −36 | −26 |
| | Ventral anterior Insula | | R | 129 | 3.84 | 38 | −6 | −14 |
| | Medial STG | | R | | 3.15 | 44 | −14 | −10 |
| | aMCC | | R | 35 | 3.70 | 6 | 14 | 38 |
| | aMCC | | L | 13 | 3.32 | −8 | 20 | 32 |
| | pACC | | R | 25 | 3.47 | 4 | 28 | 24 |
| | IPL | | L | 22 | 3.54 | −66 | −38 | 26 |

Note:
All regions exceed height threshold corresponding to P <0.001 (uncorrected).
Coordinates (in standard Montreal Neurological Institute [MNI] space) refer to maximally activated foci:
x = distance (mm) to the right (+) or the left (−) of the midsagittal line;
y = distance anterior (+) or posterior (−) to the vertical plane through the anterior commissure (AC);
z = distance above (+) or below (−) the inter-commissural (AC-posterior commissure (PC)) line.
L and R refer to the left and right hemisphere, respectively.

GEOS Category with Respect to Hedonicity Alone

Having mapped those neural networks that are sensitive to the pleasantness of odors, it was tested whether there were brain regions whose activity could be better explained by each GEOS category with respect to hedonicity alone. In particular, it was postulated that, if the GEOS is a more accurate model of the neural representation of olfactory-elicited feelings, then reliable portions of the neural network that are sensitive to odorants might exhibit signals specific for GEOS categories, over and above the putative effects of hedonicity.

associated with Pleasant Feeling (PF>H), whereas Unpleasant Feeling (UF>H) implicated a network that was very similar to that of H−, with the additional presence of the amygdala, precuneus, and 2 clusters spanning from the MFG to the superior frontal gyms (SFG), bilaterally. No effects were associated with the inverse contrast (H>category), except for the UF category (see FIG. 5, black blobs, and Table 5 for details). Of note is that, unlike the case of other GEOS categories, the results associated with Unpleasant Feeling might be confounded, as participants' ratings from this category were decorrelated with those of hedonicity.

TABLE 5

Areas correlating with individual ratings of categories > HEDO or HEDO > categories

| Contrast | Region | Extends to | Lat. | Cl. Size | z value | x | y | z |
|---|---|---|---|---|---|---|---|---|
| SP > H | MTG | ITG/IFG | R | 24 | 3.65 | 56 | −24 | −20 |
|  | Ventral anterior insula |  | R | 30 | 3.57 | 38 | 4 | −12 |
|  | lateral OFC |  | L | 8 | 3.38 | −28 | 44 | −14 |
| RF > H | MTG |  | R | 5 | 3.28 | 58 | −32 | 10 |
|  | STG |  | L | 6 | 3.27 | −62 | −4 | 0 |
| RX > H | Cerebellum vermis |  | L | 4 | 3.23 | −2 | −62 | −28 |
|  | PostCG |  | L | 5 | 3.21 | −26 | −38 | 54 |
| DE > H | IFG | Ant. insula/OFC | R | 36 | 3.62 | 32 | 30 | −4 |
|  | MEG |  | R | 6 | 3.32 | 46 | 8 | 42 |
|  | PostCG |  | R | 6 | 3.47 | 30 | −38 | 46 |
|  | Insular claustrum |  | L | 4 | 3.36 | −32 | −12 | 12 |
|  | STG |  | R | 4 | 3.15 | 56 | −28 | 14 |
| UF > H | IFG | PreCG | R | 102 | 4.07 | 62 | 8 | 26 |
|  | SEG/SMA |  | R | 203 | 4.36 | 12 | 8 | 62 |
|  | SEG | MEG/dlPFC | L | 62 | 3.59 | −26 | 46 | 30 |
|  | SFG/dlPFC |  | R | 42 | 3.48 | 18 | 44 | 32 |
|  | SFG/dlPFC |  | R |  | 3.25 | 24 | 48 | 26 |
|  | MFG/dlPFC |  | R |  | 3.25 | 36 | 46 | 34 |
|  | STG/planum polare | Ventral insula | R | 295 | 3.99 | 38 | −6 | −14 |
|  | Anterior insula |  | R |  | 3.98 | 40 | 10 | −6 |
|  | PHG | Amyg. | L | 14 | 3.32 | −22 | −6 | −28 |
|  | PHG | Amyg. | L |  | 3.15 | −30 | −2 | −24 |
|  | pACC |  | R | 159 | 3.76 | 4 | 28 | 24 |
|  | aMCC |  | L |  | 3.65 | −8 | 20 | 32 |
|  | aMCC |  | R |  | 3.30 | 10 | 28 | 30 |
|  | aMCC |  | R | 20 | 3.47 | 6 | 14 | 38 |
|  | pMCC |  | R | 5 | 3.25 | 8 | −24 | 42 |
|  | Cerebellum anterior lobe | Pons | R | 133 | 3.94 | 4 | −44 | −28 |
|  | Cerebellum anterior lobe |  | L | 11 | 3.42 | −16 | −36 | −26 |
|  | Precuneus |  | R | 8 | 3.18 | 2 | −74 | 32 |
| H > UF | MTG | Hipp | L | 18 | 3.90 | −38 | −22 | −14 |
|  | ITG |  | R | 11 | 3.29 | 54 | −52 | −14 |

Note:
All regions exceed height threshold corresponding to $P < 0.001$ (uncorrected).
Coordinates (in standard Montreal Neurological Institute [MNI] space) refer to maximally activated foci:
x = distance (mm) to the right (+) or the left (−) of the midsagittal line;
y = distance anterior (+) or posterior (−) to the vertical plane through the anterior commissure (AC);
z = distance above (+) or below (−) the inter-commissural (AC-posterior commissure (PC)) line.
L and R refer to the left and right hemisphere, respectively.
pMCC refers to posterior middle cingulate cortex.

Figure 5:
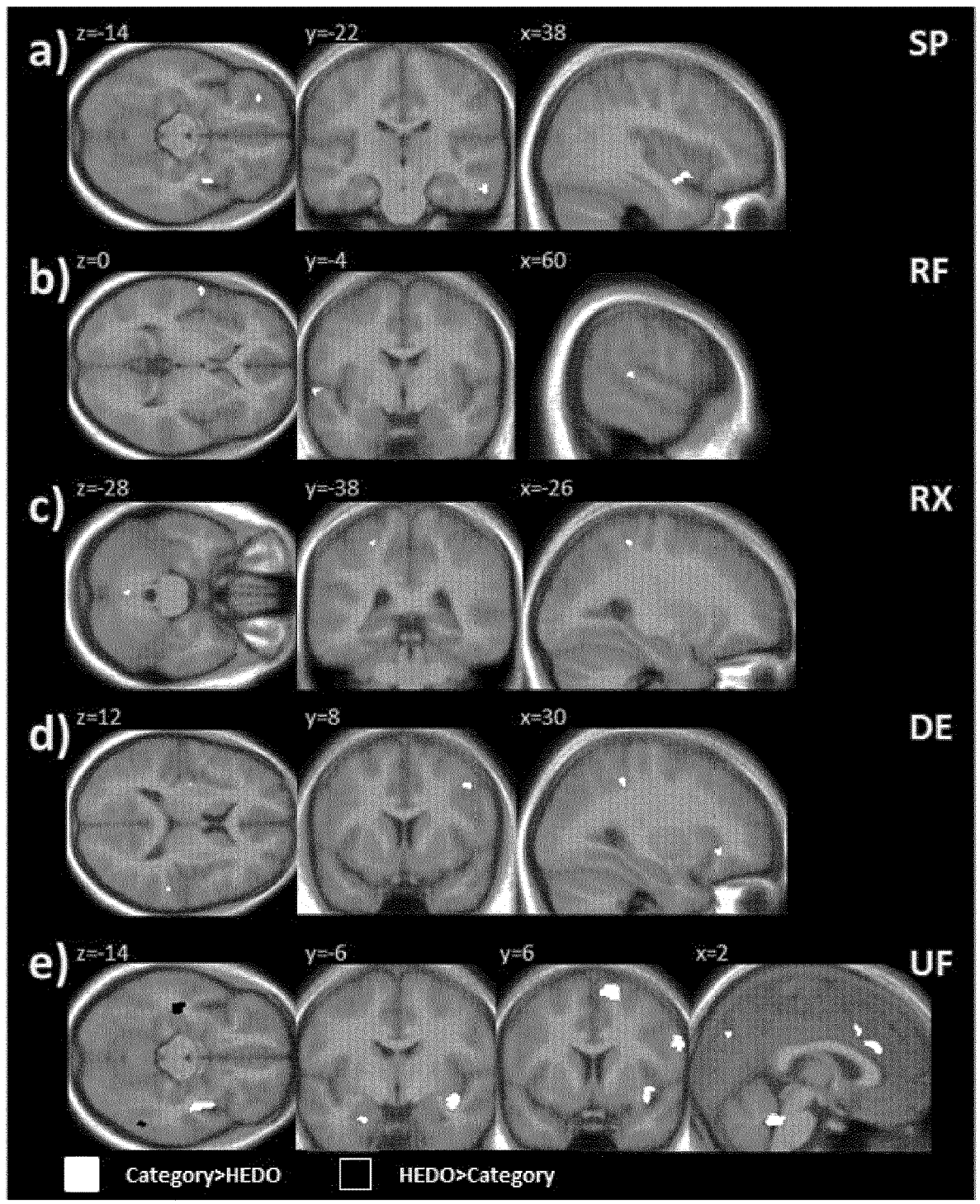
FIG. 5 represents the regression analysis for GEOS categories compared with hedonicity ratings at the second level. GEOS parametrical category activations were contrasted with hedonicity parametrical activations. Whole brain (WB), P=0.001, uncorrected.

All the results from this analysis are shown in FIG. 5 (white blobs) and Table 5. Sensory Pleasure (SP) had better explicatory power than did hedonicity (SP>H) in the activity of the left lateral OFC, together with the right ventral anterior insula and the middle temporal gyms (MTG), extending to the inferior frontal and temporal gyri (IFG/ITG). The bilateral insula was also implicated in "Desire-Sensuality" (DE>H), in combination with the postcentral gyms (postCG), IFG, middle frontal gyms (MFG), and STG. Relaxation (RX>H) was also associated with the postCG and cerebellum, whereas Refreshing (RF>H) implicated only the temporal areas (STG and MFG). No effects were Taken together, these results confirm that, although an odor's valence is a relevant feature of neural olfactory processing, brain representations of odor-evoked feelings are not limited to hedonicity, but do also involve properties such as sensory pleasure, sensuality, and relaxation.

Specific Effects of Individual Feeling Categories

To determine whether specific feelings were associated with differentiated neural correlates, each GEOS category against all others (e.g. SP>mean(DE, RX, RF, PF, UF) or SP>GEOS) were compared. See FIG. 6 and Table 6 for full results.

TABLE 6

Areas correlating with individual ratings of categories > GEOS or GEOS > categories

| Contrast | Region | Extends to | Lat. | Cl. Size | z value | x | y | z |
|---|---|---|---|---|---|---|---|---|
| SP > GEOS | Lateral OFC | | L | 21 | 3.48 | −32 | 42 | −14 |
| RX > GEOS | Middle frontopolar g. | SFG | L | 83 | 3.95 | −20 | 60 | 8 |
| | IFG/vlPFC | | L | 15 | 3.25 | −34 | 44 | 4 |
| | PostCG | Supramarginal. g. | R | 20 | 3.58 | 36 | −34 | 56 |
| | Fusiform g. | | L | 11 | 3.50 | −26 | −44 | −16 |
| | MTG | | L | 12 | 3.26 | −62 | −12 | −10 |
| DE > GEOS | ITG | | R | 4 | 3.25 | 48 | −44 | −16 |
| | IFG/Lateral OFC | Anterior insula | R | 5 | 3.24 | 30 | 30 | −4 |
| UF > GEOS | SFG/SMA | | R | 178 | 4.15 | 12 | 8 | 62 |
| | IFG/PreCG | | R | 43 | 3.68 | 62 | 10 | 26 |
| | MEG/frontopolar PEC | | L | 74 | 3.63 | −28 | 48 | 30 |
| | STG/Planum polare | | R | 59 | 3.66 | 44 | −14 | −10 |
| | Ventral insula | | R | | 3.56 | 38 | −6 | −14 |
| | Anterior Insula | | R | 24 | 3.60 | 40 | 10 | −6 |
| | PHG | Hipp./Amygdala | L | 21 | 3.54 | −22 | −6 | −28 |
| | pACC | | R | 53 | 3.54 | 4 | 28 | 24 |
| | aMCC | | L | 39 | 3.48 | −6 | 20 | 32 |
| | aMCC | | R | 7 | 3.20 | 4 | 14 | 38 |
| | Brainstem | | R | 49 | 3.50 | 6 | −8 | −16 |
| | Cerebellum posterior lobe | | L | 8 | 3.65 | −48 | −48 | −40 |
| | Cerebellum anterior Lobe | Pons | R | 41 | 3.44 | 2 | −44 | −28 |
| GEOS > SP | SFG/SMA | | R | 41 | 4.06 | 10 | 6 | 60 |
| GEOS > RX | Amygdala | | L | 17 | 3.55 | −20 | −4 | −26 |
| | Olfactory trigone | | R | 16 | 3.52 | 18 | 8 | −14 |
| GEOS > DE | pACC | | R | 15 | 3.37 | 0 | 28 | 18 |
| GEOS > PF | STG | Hipp./Ventral insula | R | 42 | 3.52 | 42 | −10 | −12 |
| | ITG | | R | 8 | 3.50 | 54 | −74 | 12 |
| | Ventral insula | | R | 26 | 3.39 | 38 | 6 | −12 |
| | Anterior Insula | | L | 5 | 3.16 | −26 | 18 | 4 |
| | aMCC | | R | 17 | 3.47 | 10 | 26 | 30 |
| GEOS > UF | MTG | | L | 31 | 4.11 | −38 | −22 | −14 |
| | Hipp. | | L | | 3.15 | −30 | −28 | −10 |
| | Hipp. | | R | 5 | 3.30 | 34 | −34 | −6 |
| | IFG | | R | 41 | 3.58 | 54 | −52 | −14 |

Note:
All regions exceed height threshold correspondingto P <0.001 (uncorrected).
Coordinates (in standard Montreal Neurological Institute [MNI] space) refer to maximally activated foci:
x = distance (mm) to the right (+) or the left (−) of the midsagittal line;
y = distance anterior (+) or posterior (−) to the vertical plane through the anterior commissure (AC);
z = distance above (+) or below (−) the inter-commissural (AC-posteriorcommissure (PC)) line.
L and R refer to the left and right hemisphere, respectively. g. refers to gyrus.

The left lateral OFC exhibited a larger increase in activity with SP as opposed to the other categories (SP>GEOS). On the other hand, right SMA activity was negatively coupled with SP (GEOS>SP). RX exhibited positive activity modulations in the middle frontopolar gyms, ventrolateral PFC (vlPFC), SFG, MTG, and fusiform gyms, as well as the postCG, extending to the supramarginal gyms (RX>GEOS). Interestingly, negative modulations of brain activity (GEOS>RX) were found in right olfactory trigone and the left amygdala. DE was associated with positive effects in the IFG (extending to the anterior insula) and the ITG (DE>GEOS) and with negative effects in the perigenual anterior cingulate gyms (pACC) (GEOS>DE). No suprathreshold positive or negative effects were found for RF.

Figure 6:
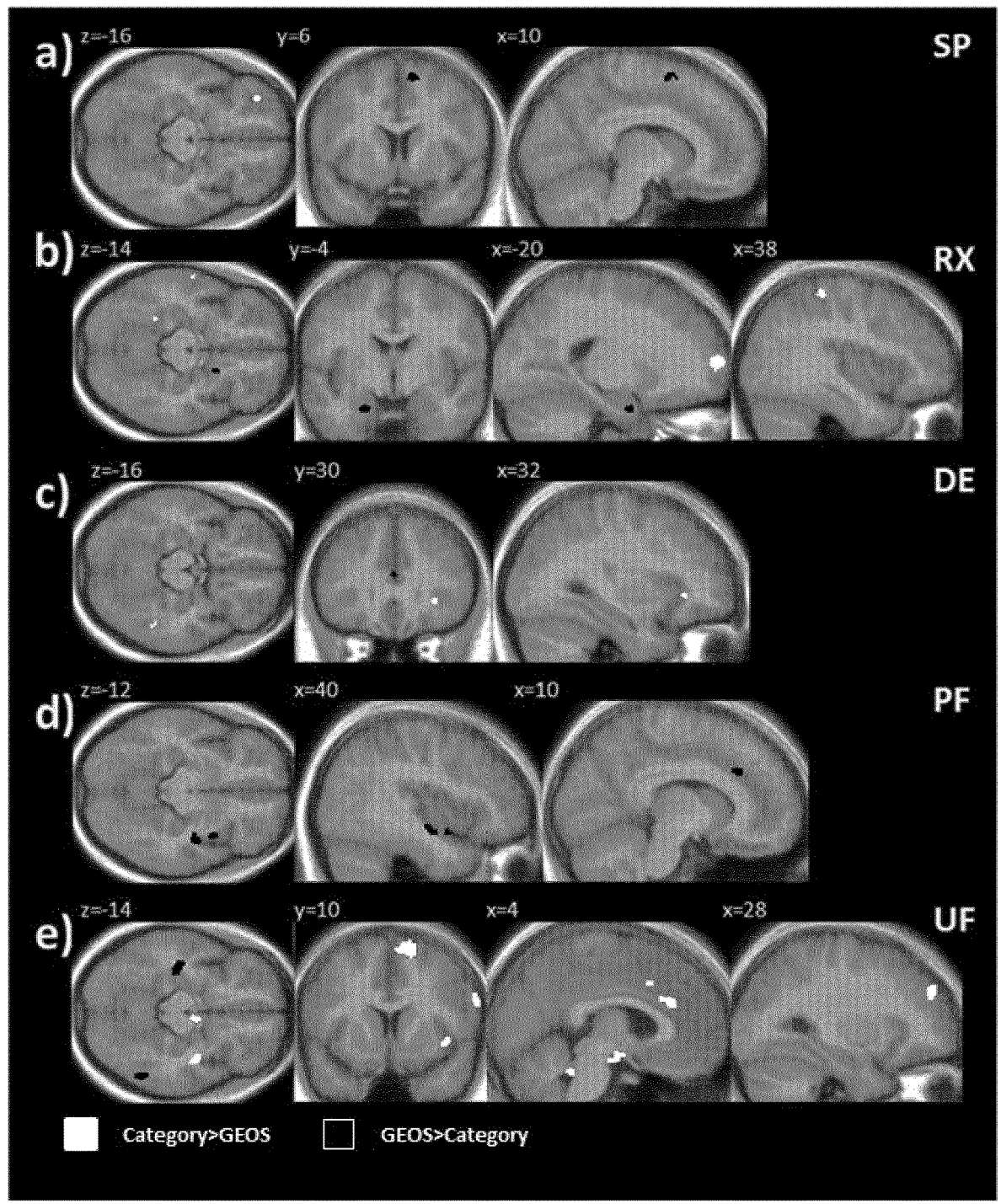
FIG. 6 represents the regression analysis for individual categories compared with the rest of GEOS at the second level. Individual GEOS category parametrical activations are contrasted for each specific emotion compared to the other remaining GEOS categories. Whole brain (WB), P=0.001, uncorrected.

Finally, as shown in FIG. 6 d,e, the analysis of PF and UF components implicated a network that is highly reminiscent of that implicated in the analysis of hedonicity (for both UF>GEOS and GEOS>PF contrasts). This suggests that these 2 categories describe information about the olfactory-elicited affect that mostly overlaps with pleasantness, with additional activations in the cerebellum, hippocampus, amygdala, or midbrain for UF.

Although the odor-elicited feelings categories described by GEOS are partially correlated given their common hedonic tone, these comparisons reveal specific effects of a given feeling regressor that is different from the single or combined effects of other feelings. Overall, these imaging results stress the unique contribution of each emotional category, which is illustrated by a specific neural pattern.

Effects of Intensity and Familiarity

Figure 7:
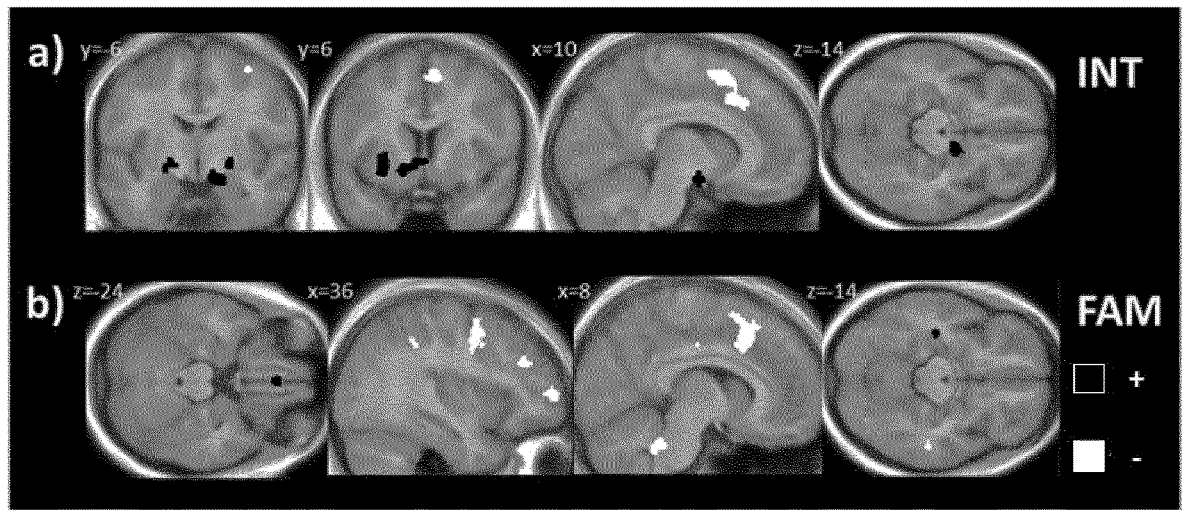
FIG. 7 represents the regression analysis for intensity and familiarity at the second level. Whole brain (WB), P=0.001, uncorrected.

Finally, given that intensity (I) and familiarity (F) are traditionally used together with hedonicity (H) for odor characterization, the corresponding neural correlations by performing group-level one-sample t-tests were also examined (see FIG. 7 and Table 7 for full results).

TABLE 7

Areas correlating with intensity (I) and familiarity (F) ratings

| Contrast | Region | Extends to | Lat. | Cl. Size | z value | x | y | z |
|---|---|---|---|---|---|---|---|---|
| I+ | Amygdala/Hipp | PHG/PostPirC./EC | R | 100 | 4.06 | 14 | −6 | −16 |
|  | Lateral glob. pall. |  | R | 36 | 4.06 | 24 | −8 | −6 |
|  | Lateral glob. pall. | Caudate | L | 167 | 3.85 | −12 | 4 | −6 |
|  | Medial glob. pall. |  | L |  | 3.34 | −18 | −6 | −6 |
|  | Putamen |  | L | 99 | 3.54 | −28 | 4 | 2 |
|  | Putamen |  | R | 34 | 3.35 | 18 | 14 | −8 |
| I− | SMA |  | R | 336 | 4.66 | 10 | 8 | 54 |
|  | aMCC |  | R |  | 3.69 | 10 | 20 | 40 |
|  | MFG/SMA |  | R | 16 | 3.42 | 34 | −6 | 58 |
|  | MFG/PreCG |  | R | 6 | 3.25 | 36 | 2 | 48 |
| F+ | Hipp. |  | L | 17 | 3.76 | −38 | −22 | −16 |
|  | mOFC/Gyrus rectus |  | R | 29 | 3.49 | 0 | 34 | −20 |
| F− | Medial SFG | MCC | R | 315 | 4.06 | 10 | 16 | 40 |
|  | SMA |  | R |  | 3.83 | 6 | 18 | 48 |
|  | Lateral SFG/SMA |  | R |  | 3.81 | 12 | 12 | 54 |
|  | MFG |  | R | 242 | 4.02 | 40 | 36 | 28 |
|  | MFG/Inferior frontal operculum |  | R |  | 3.68 | 54 | 22 | 32 |
|  | MFG |  | R | 148 | 3.94 | 34 | 2 | 46 |
|  | MFG/PreCG |  | R |  | 3.39 | 38 | 0 | 38 |
|  | MFG/SMA |  | R |  | 3.31 | 38 | 8 | 54 |
|  | PreCG |  | R | 144 | 3.67 | 48 | 2 | 22 |
|  | IFG pars opercularis |  | R |  | 3.54 | 50 | 8 | 36 |
|  | Ant. MFG |  | R | 78 | 3.58 | 36 | 54 | 6 |
|  | Ant. PEC/frontopolar |  | R |  | 3.24 | 28 | 52 | 8 |
|  | Lat. OFC |  | R |  | 3.23 | 40 | 46 | 2 |
|  | Inferior frontal operculum |  | R | 7 | 3.29 | 38 | 12 | 24 |
|  | Anterior insula | IFG pars triangularis | R | 26 | 3.73 | 32 | 28 | 6 |
|  | Lateral MTG |  | R | 15 | 3.48 | 54 | −26 | −14 |
|  | ITG |  | R | 8 | 3.46 | 44 | −2 | −30 |
|  | STG |  | R | 9 | 3.28 | 48 | −18 | −10 |
|  | PCC |  | L | 9 | 3.43 | −14 | −28 | 38 |
|  | IPL/Supramarginal g. |  | R | 23 | 3.52 | 36 | −40 | 42 |
|  | IPL/Supramarginal g. |  | R | 29 | 3.29 | 58 | −38 | 34 |
|  | Pons |  | R | 5 | 3.41 | 12 | −28 | −30 |
|  | Cerebellum culmen |  | L | 579 | 4.20 | −20 | −66 | −34 |
|  | Cerebellum anterior lobe |  | R | 122 | 4.14 | 8 | −40 | −30 |
|  | Cerebellum posterior lobe |  | L | 4 | 3.13 | −34 | −74 | −40 |

Note:
All regions exceed height threshold corresponding to $P < 0.001$ (uncorrected).
Coordinates (in standard Montreal Neurological Institute [MNI] space) refer to maximally activated foci:
x = distance (mm) to the right (+) or the left (−) of the midsagittal line;
y = distance anterior (+) or posterior (−) to the vertical plane through the anterior commissure (AC);
z = distance above (+) or below (−) the inter-commissural (AC-posterior commissure (PC)) line.
L and R refer to the left and right hemisphere, respectively.
PCC and glob. pall. refer to posterior cingulate cortex and globus pallidus, respectively.

Intensity was positively correlated with activity in the right amygdala-hippocampus, extending to the parahippocampal area (PHG), the entorhinal cortex (EC), and the posterior piriform cortex (FIG. 7a, black blobs, and Table 7), in line with the previous results obtained for the O>NO contrast. This pattern of activation corresponds to primary and secondary olfactory areas (see Results section, main effect of olfactory stimulation, positive and negative odors). In addition, high intensity also induced activations in the bilateral pallidum and putamen (FIG. 7a, black blobs), whereas low intensity correlated with the SMA, precentral gyms (PreCG), and anterior middle cingulate gyms (aMCC) (FIG. 7a, white blobs).
Familiar odors elicited activity in the left hippocampus, involved in odor quality and memory (Savic et al., 2000), and in the gyms rectus (FIG. 7b, black blobs). Unfamiliar odors (FIG. 7b, white blobs) implicated a network similar to that isolated with low hedonicity (i.e. the SMA, cingulate gyms, dlPFC (BA9), insula, and cerebellum). Furthermore, the perception of unfamiliar odors recruited the MTG and the MFG.

Conclusions

The parametric analysis used in the method of the present invention specifically takes into account parametric intensity variations between odorants and idiosyncratic differences between participants, unlike the latter studies that used pre-defined and fixed stimulus sets.

The method of the present invention enables one to identify the neural correlates of specific emotion categories reported during odor perception, beyond the dimensions of valence or arousal as traditionally investigated in past fMRI studies.

Furthermore, the use of the parametric approach to assess brain response according to the magnitude of felt emotions, allows to account not only for fine-grained distinctions and mixtures in subjective feelings (with a given odor being rated along multiple emotion types simultaneously), but also for the large interindividual variability in affective responses (with the same odor eliciting different emotions in different people as a function of personal factors and cultural backgrounds).

Differential activation profiles in distributed cortico-subcortical networks were observed for feelings of Sensory Pleasure, Relaxation, Desire, in addition to Pleasant and Unpleasant feelings, which were distinct not only from each other but also from the more global dimensions of Hedonicity or Intensity.

All these data underline the correlation of specific brain activation patterns with the feelings categories (defined by descriptors) revealed by declarative methods and further highlight the fact each of these emotional patterns is rooted in a specific brain activation pattern.

Comparative Example 2

Odor with Similar Valence Ratings

Figure 8:
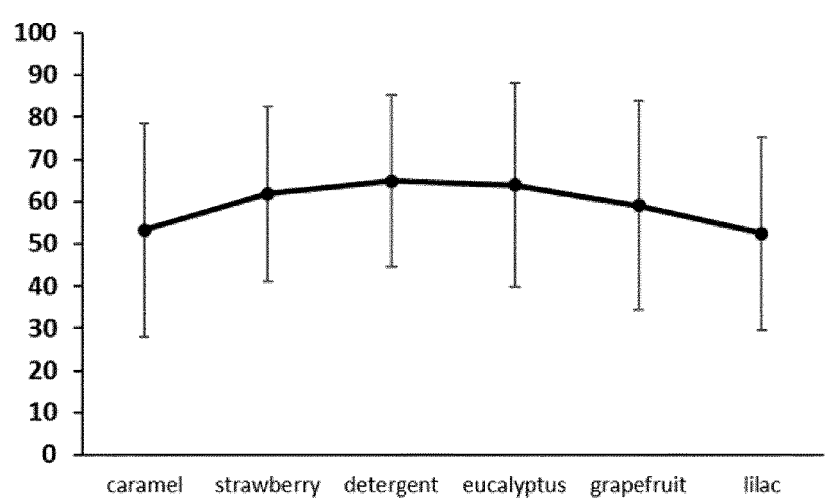
FIG. 8 represents mean valence ratings for different odorants.

Data obtained from example 1 were used and the valence of 6 odorants (caramel, strawberry, detergent, eucalyptus, grapefruit and lilac) was determined. Their valence ratings were not statistically different $F(5,80)=1.34$; $p=0.25$, $\eta_p^2=0.07$ (see FIG. 8).

Feelings ratings obtained in response to those odorants similar in valence were then subjected to hierarchical cluster analysis by using Ward's method.

Figure 9:
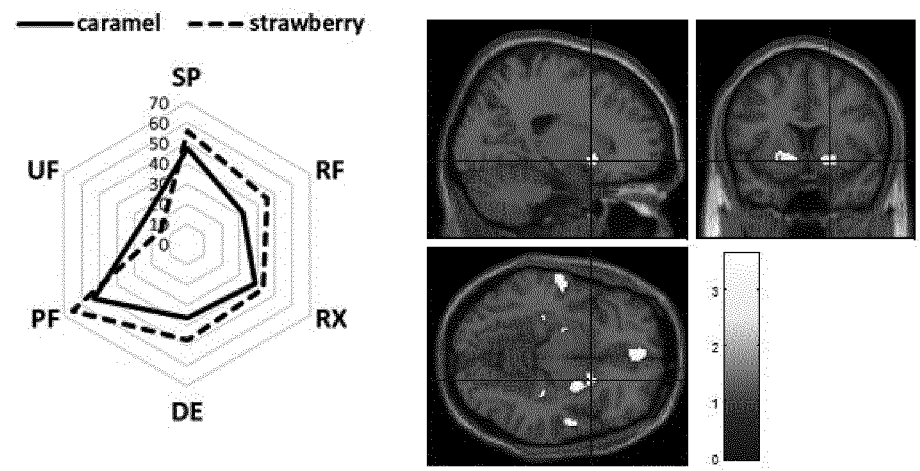
FIG. 9-11 represent feelings' specific clusters with their associated activated brain network.
Figure 10:
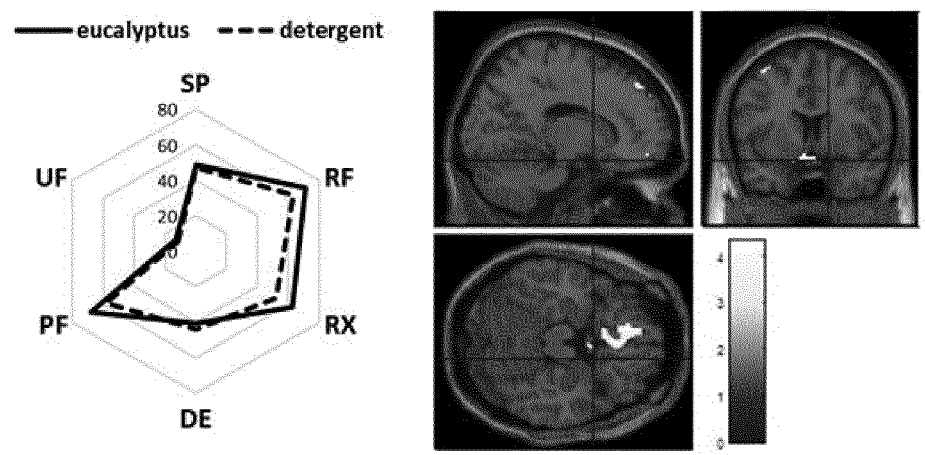
Figure 11:
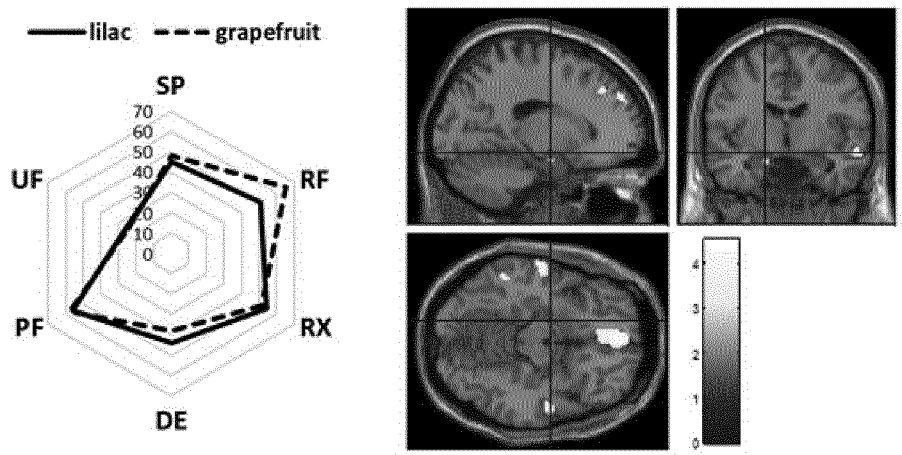

This analysis led to 3 different clusters which were composed of caramel and strawberry (cluster A—see FIG. 9), eucalyptus and detergent (cluster B—see FIG. 10) and caramel and grapefruit (cluster C—see FIG. 11).

The brain response associated with each cluster was determined and compare to no odor condition and revealed different brain networks for each cluster.

One can conclude from this example that odors with similar valence ratings (i.e. odors that are reported as similarly pleasant by the group of participants) not only differ in the feelings they elicit (represented by cluster A, B and C) but also evoke different brain networks.

The invention claimed is:

1. A method for determining at least two brain activation patterns related to at least two elicited feelings for a group of subjects smelling odorants, said method comprising the following steps:
  (i) Providing at least two odorants;
  (ii) Submitting a group of subjects to at least two odorants, each in turn, in a MRI scanner;
  (iii) Performing functional Magnetic Resonance Imaging (fMRI) of the brain of each subject smelling each odorant in turn to determine a brain activation to each odorant for each subject,
  (iv) Optionally, reiterating step (iii) and identifying an average brain response to each odorant,
  (v) Once step (iii) or (iv) is completed, submitting the group of subjects to an evaluation of feelings evoked by each odorant based on a declarative method, wherein a perceived intensity of at least two feeling descriptors are rated on a continuous scale;
  (vi) Rating and averaging the perceived intensity of the at least two feeling descriptors reported by the group of subjects for each odorant based on said declarative method, wherein the feeling descriptors are not restricted to the affective dimension of valence, thereby obtaining descriptor rating scores,
  (vii) Performing a statistical method using the descriptor rating scores obtained in step (vi) across the odorants to obtain a brain activation pattern associated to each descriptor;
  wherein feelings evoked by the at least two odorants are defined by at least 6 descriptors.

2. The method according to claim 1, wherein the statistical method in step (vii) is a parametric regression analysis.

3. The method according to claim 1, wherein the method comprises a further step of preprocessing of MRI data before step (vii) and wherein the step of preprocessing comprises the following steps:
  (i) realignment of the MRI images to a reference scan,
  (ii) mapping each coordinate of individual brains onto the corresponding coordinates of a standard brain template, and
  (iii) smoothing the images.

4. The method according to claim 1, wherein the group of subjects is submitted to at least 5 odorants.

5. The method according to claim 1, wherein the descriptors are chosen from the group consisting of sensory pleasure (SP), refreshing (RF), relaxation (RX), desire-sensuality (DE), pleasant feeling (PF), unpleasant feeling (UF), familiarity (F), hedonicity (H) and intensity (I).

6. The method according to claim 1, wherein each of the at least two odorants comprises a perfume in the form of a perfuming ingredient alone or in the form of a perfuming composition including a mixture of perfuming ingredients.

7. The method according to claim 1, wherein the declarative method used in step (v) is GEOS (Geneva Emotional Odor Scale).

8. The method according to claim 1, wherein the group of subjects comprises at least 5 subjects.

9. The method according to claim 1, wherein step (ii) is carried out by an olfactometer.

10. A method for generating a perfuming composition that elicits a specific odor-elicited feeling in a subject, the method comprising the steps of:
  a. receiving, by at least one computer processor executing specific programmable instructions configured for the method, data comprising at least one specific odor-elicited feeling elicited by a perfuming raw ingredient from a plurality of perfuming raw ingredients;
  b. receiving, by the at least one computer processor, input data comprising a specific odor-elicited feeling from the subject;
  c. selecting, by the at least one computer processor, based in the input data, at least one perfuming raw material that elicits the specific odor-elicited feeling; and
  d. formulating, based on the selection, by the at least one computer processor, the perfuming composition that elicits the specific odor-elicited feeling in the subject, wherein the method comprises generating the data comprising at least one specific odor-elicited feeling elicited by a perfuming raw ingredient from a plurality of perfuming raw ingredients by the method according to claim 1.

11. The method according to claim 1, wherein the group of subjects is submitted to at least 10 odorants.

12. The method according to claim 1, wherein feelings evoked by the at least two odorants are defined by at least 9 descriptors.

13. The method according to claim 1, wherein the group of subjects comprises at least 10 subjects.

14. The method according to claim 1, wherein the group of subjects comprises at least 15 subjects.

15. A method enabling the identification of at least one brain activation pattern corresponding to a specific feeling category elicited by an odorant, the method comprising using the method as defined in claim 1.

* * * * *